United States Patent [19]

Golberstein

[11] Patent Number: 5,113,082
[45] Date of Patent: May 12, 1992

[54] ELECTRO-OPTICAL INSTRUMENT WITH SELF-CONTAINED PHOTOMETER

[76] Inventor: Moshe Golberstein, 2100 Drew Ave. South, Minneapolis, Minn. 55416

[21] Appl. No.: 580,824

[22] Filed: Sep. 11, 1990

[51] Int. Cl.$^5$ .............................................. G01N 21/86
[52] U.S. Cl. ....................................... 250/571; 356/445
[58] Field of Search ............... 250/571, 572, 560, 561; 356/371, 375, 376, 446, 445

[56] References Cited

U.S. PATENT DOCUMENTS

| | | | |
|---|---|---|---|
| 3,692,414 | 9/1972 | Hosterman et al. | 356/375 |
| 3,918,816 | 11/1975 | Foster et al. | 356/375 |
| 4,204,725 | 5/1980 | Balasubraminson | 356/376 |
| 4,548,504 | 10/1985 | Morander | 356/375 |
| 4,552,458 | 11/1985 | Lowne | 356/446 |
| 4,589,773 | 5/1986 | Ido et al. | 356/371 |
| 4,622,502 | 11/1986 | Maruo | 318/640 |
| 4,647,209 | 3/1987 | Neukomm et al. | 356/376 |
| 4,676,653 | 6/1987 | Strohmeier et al. | 356/446 |
| 4,767,934 | 8/1988 | Stauffer | 250/561 |
| 4,770,536 | 9/1988 | Golberstein | 356/371 |
| 4,775,235 | 10/1988 | Hecker et al. | 356/375 |
| 4,782,239 | 11/1988 | Hirose | 250/561 |
| 4,789,243 | 12/1988 | Mathew | 356/375 |
| 4,808,003 | 2/1989 | Kessels | 356/376 |
| 4,874,246 | 10/1989 | Den Boef | 356/375 |

Primary Examiner—David C. Nelms
Assistant Examiner—Stephone B. Allen
Attorney, Agent, or Firm—James V. Harmon

[57] ABSTRACT

An optical instrument for measuring characteristics of a specimen comprises a light source and an axial reflective member spaced from the light source to define an optical axis for the instrument along a line between the light source and the reflective member. A non-axial reflector is positioned laterally of the reflective member and laterally of the optical axis to receive a beam reflected from the axial reflective member. The non-axial reflector is oriented to reflect the beam onto the specimen. The instrument also contains a segmented photosensor and a second non-axial reflector to receive the beam reflected from the specimen and reflect it onto the segmented photosensor. The photosensor is positioned in the instrument to receive the beam from the second non-axial reflector. A conductor connected to each segment of the photosensor is provided for carrying current to signal conditioning hardware used to compare the current from the segments of the photosensor to provide information concerning the specimen.

29 Claims, 2 Drawing Sheets

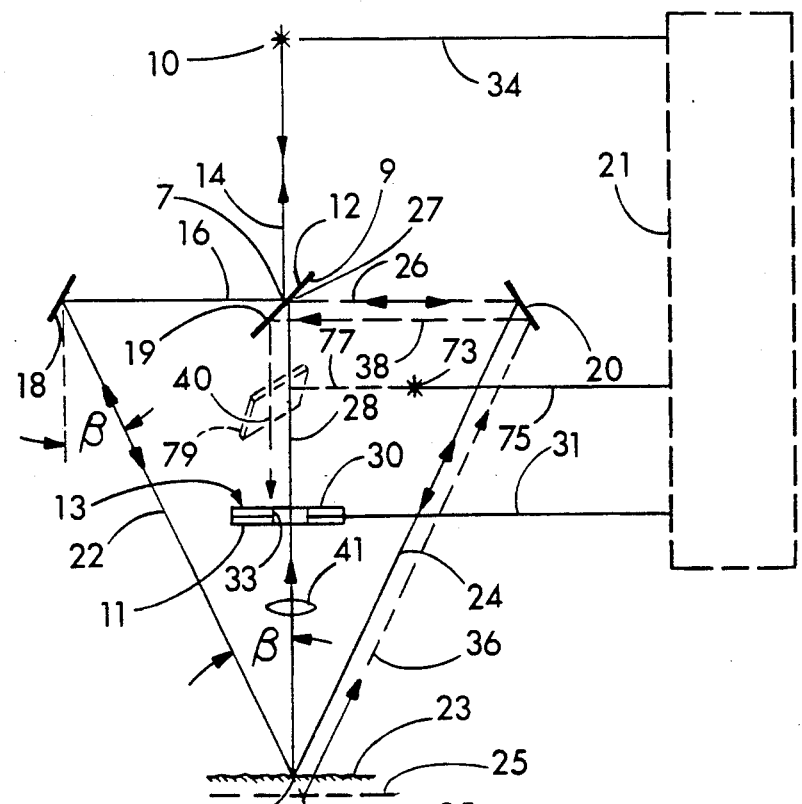
FIG. 1
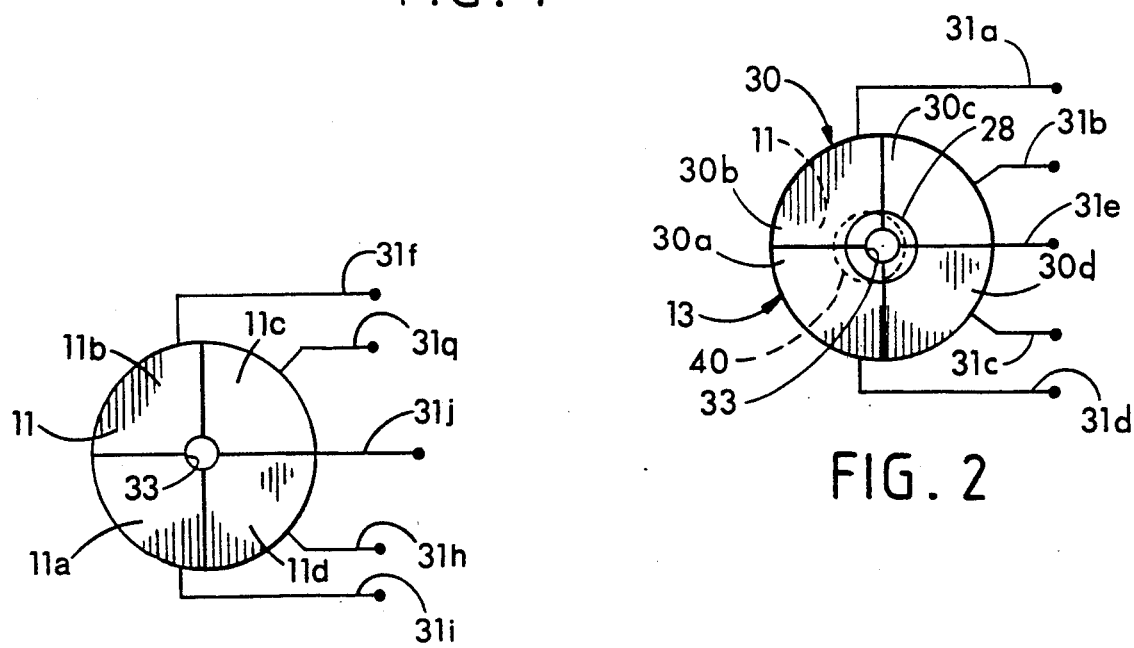
FIG. 2A
FIG. 2

ELECTRO-OPTICAL INSTRUMENT WITH SELF-CONTAINED PHOTOMETER

FIELD OF THE INVENTION

The present invention relates to optical instrumentation and more particularly to optical instruments for conducting measurements for example measurements from reflective surfaces.

BACKGROUND OF THE INVENTION

There are many methods currently in use to measure surface reflectance and surface roughness. Some methods were described in the background paragraph of my prior U.S. Pat. No. 4,770,536. Other methods are based upon triangulation and interferometric principles. While the Reflective Photometry Instrument described in U.S. Pat. No. 4,770,536 does measure reflectance, its performance is further enhanced by introduction of additional features to be described below. One major objective of of the present invention is to provide a controllable distance, e.g. a constant distance, and if desired, a constant angle between the instrument and the surface under examination at which surface reflectance or emission can be measured.

SUMMARY OF THE INVENTION

Briefly, the invention provides an optical instrument for measuring characteristics of a specimen. The instrument includes a light source, an axial reflective member spaced from the light source to define an optical axis for the instrument along a line between the light source and the reflective member. A non-axial reflector is positioned laterally of the reflective member and laterally of the optical axis to receive a beam reflected from the axial reflective member. The non-axial reflector is oriented to reflect the beam onto the specimen. A photosensor is provided in the instrument. The photosensor is positioned in the instrument to receive the beam from the specimen. Means such as conductors are provided for carrying signals from the photosensor to signal conditioning hardware which functions to provide information concerning the specimen responsive to the signals from the photosensor. Preferably, a second non-axial reflector is provided to receive the beam reflected from the specimen and in turn to reflect it onto the photosensor. The second non-axial reflector is positioned to receive the beam reflected from the specimen originating from the first non-axial mirror.

While not essential, it is preferred that the photosensors are segmented to provide additional information concerning the surface being studied, particularly since it is difficult to be certain in all cases that the light beam is normal to the surface of the photosensor. It is also preferred that the photosensor is apertured to allow a portion of the incident beam to pass through the photosensor.

DESCRIPTION OF THE PREFERRED EMBODIMENTS

More specifically, one preferred form of the invention provides a non-contact instrument for determining a distance between a reference point typically within the instrument and a test or target surface, i.e. the surface of a workpiece. Such a distance will be referred to herein as a "standoff distance." Once the instrument is positioned at a known standoff distance from the target surface or workpiece, it can then measure the reflectance of the surface, for example as described using prior U.S. Pat. No. 4,770,536. An instrument made according to the present invention can be made to utilize either of two modes of operation. One mode is based upon reflective/refractive optics principles. The other is based upon interferometric principles. The physical embodiment of instruments utilizing these two different principles are similar in architecture and employ most of the same components. The components common to both instruments are: a collimated light source to provide a longitudinal or axial beam defining an optic axis, preferably at least two non-axial mirrors to receive the beam reflected laterally from the axial beam, and a photosensor. In a prefered form of the invention, the photosensor is an apertured, double-sided radially segmented photosensor. The instrument is connected during use to suitable signal conditioning hardware.

In addition to the above mentioned components, when the instrument is to use reflective/refractive principles it contains an axially located double-sided mirror. On the other hand, when the instrument is to employ interferometric principles, an axial beam splitter is used in place of the axial mirror and an additional apertured radially segmented photosensor is provided. Both the mirror and beam splitter comprise axial reflective members. The light source for an interferometric instrument is a coherent monochromatic source with known polarization characteristics. The interferometric instrument utilizes a combination of different beam paths to produce interfering beams which are detected by the photosensors.

Performance of both types of instruments can be further improved, if desired, by additional lenses and other components known in the art. By way of example, such optional components include quarter wave plates, polarizers, additional isolators (Faraday type, for example), drivers for lenses, micrometric displacement of mirror (such as PZT translators for example), and shutters. The instrument of the present invention has an internal dimensional reference point that is established by the longitudinal axial beam and its intersection with the double-sided mirror or the beam splitter, as the case may be. Major components of the instrument are set at predetermined distances from this point.

When the longitudinal axial beam emanating from the light source encounters the first surface, i.e., the upper surface, of the double-sided mirror, it is deflected toward one of the non-axial mirrors. This second mirror is fixed at an inclined angle in such a way that the beam deflected by it to the target surface under evaluation so as to form an angle $\beta$ in relation to the surface under evaluation. The surface under evaluation deflects the beam toward a third mirror (the second non-axial mirror) which is positioned laterally of the double-sided mirror. The third mirror is positioned in such a way that it establishes a selected angle between the beam reflected from the target surface under evaluation and the beam deflected from the third mirror. The beam deflected from the third mirror (the second non-axial mirror) is directed toward the opposite or second surface of the double-sided mirror (its lower surface). The second or lower surface of the double-sided mirror deflects the beam downwardly again toward the target surface along the longitudinal axis of the instrument. If the instrument is positioned at the proper standoff distance from the surface under evaluation, and the optical axis of the instrument is parallel to the normal vector of the surface under evaluation, the beam deflected downwardly from the double-sided mirror will pass through the apertured photosensor. Part of the optical power of the beam will be intercepted by the photosensor surface facing the double-sided mirror. The remaining portion will be reflected from the surface under evaluation. Part of the beam reflected from the surface under evaluation is intercepted by the apertured photosensor facing the surface under evaluation. Another portion of the beam reflected from the surface under evaluation will be deflected by the mirrors back into the light source, repeating the optical path in reverse direction. If the optical axis of the instrument is parallel to the normal of the surface under evaluation, but the distance between the instrument and the surface is different from the determined standoff distance, the light spot as intercepted by the upper side of the photosensor will be displaced on a horizontal axis, i.e. laterally across the surface of the photosensor parallel to a line between the second and third mirrors. Likewise, if the standoff distance differs from the distance to the surface under evaluation, and if the normal vector is not parallel to the longitudinal or optical axis of the instrument, the light spot on the photosensor will be displaced in the plane of the upper photosensor in a direction dictated by the amount of the deviation mentioned.

When the instrument is to utilize interferometer principles, the beam emanating from the light source passes through an upper or first apertured photosensor and is split into two parts by an axial beam splitter which replaces the double-sided mirror. One part is directed toward the target surface through an apertured photosensor. The other part is directed to the first non-axial mirror which, as mentioned, is tilted so that the beam makes an angle $\beta$ with a line normal to the target surface. From the non-axial mirror, the beam is reflected to the surface under evaluation. The surface under evaluation deflects the beam toward the second mirror from which it is deflected to the beam splitter. The beam splitter again divides the beam. One portion of the beam travels to the first mirror and, passing through the beam splitter, continues to circulate in a counterclockwise direction while subjected to periodic splits by the beam splitter. The other portion of the beam travels to the surface under evaluation through a second apertured photosensor. Two interfering beams exist in this case: one travels straight through the beam splitter from the source, while a second is subjected to periodic splits while traveling in a counterclockwise direction. A second apertured photosensor which faces the beam splitter intercepts the two interfering beams. These two beams interfere with each other as a function of difference in their respective optical paths. As the two beams are reflected from the surface under test, part of them is intercepted by the photosensor facing the surface. The reflected beams are split by a beam splitter. One part of each of the reflected beams is traveling toward the light source via an apertured photosensor above the beam splitter, and the other parts are directed toward the second mirror and will be circulating in a clockwise direction and subjected to periodic splits by the beam splitter that directs a portion of these beams to the light source via the second apertured photosensors, creating an interference pattern. The difference between the interference patterns of the two photosensors facing the beam splitter is proportional to displacement of the surface under evaluation from the standoff distance, and from deviation between a normal to the surface and the optical axis of the instrument.

In both cases (although by different methods), the signal conditioning hardware can produce the following information: the standoff distance as represented by a vector between the instrument and the surface under evaluation, and the reflectance characteristics of the surface under evaluation as a function of distance.

THE FIGURES

Refer now to the figures, which illustrate the invention by way of example.

FIG. 1 is a diagram of a distance measurement photometer in accordance with the invention when employing a reflective/refractive method;

FIG. 2 is a plan view of an apertured radially segmented photosensor assembly;

FIG. 2A is the bottom view of FIG. 2;

DETAILED DESCRIPTION OF THE INVENTION

Figure 1A:
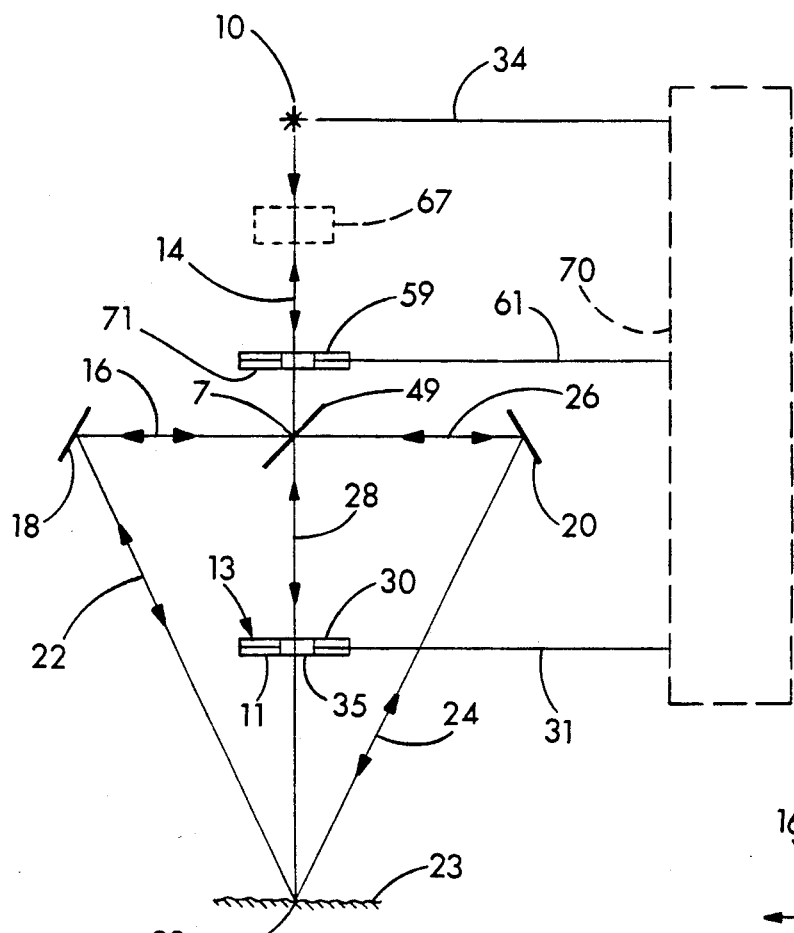
FIG. 1a is another view similar to FIG. 1 but illustrating the invention when employing photometer-interferometric principles.

The description will start with a description of the invention emloyed as a reflective/refractive distance measurement photometer instrument.

Refer now to FIG. 1. Light source 10, which can be a laser diode, a laser, a Light Emitting Diode or another collimated light source with known physical properties, projects a longitudinal axial beam identified by numeral 14 defining the optical axis of the instrument. Note that all beams are illustrated by single lines for the sake of clarity. In reality they have a certain width or profile. The longitudinal axial beam 14 encounters a double-sided mirror assembly 12, also identified by a single line. The upper mirror surface 19 of double-sided mirror 12 and the axis of beam 14 intersect. This intersection creates a point in space 7, which is a point of dimensional reference of Xo, Yo, Zo coordinates. Beam 14 is deflected from mirror surface 19 along a horizontal lateral line represented by numeral 16 to a non-axial or lateral mirror 18 which is fixed at an inclined angle $\beta$ to the optic axis 14. Mirror 18 deflects the beam along line 22 forming an angle $\beta$, to target surface 23. Target surface 23 deflects the beam along line 24 to mirror 20. A lateral mirror 20 which is positioned at a fixed angle $\beta$ with respect to the optic axis 14 deflects the beam along line 26 toward mirror surface 9 of the double-sided mirror assembly 12, forming an angle $\beta$ between mirror 20 and beam 26. From mirror surface 9, the beam is deflected along the line represented by numeral 28 through aperture 32 of photosensor assembly 30 to target surface 23.

The assembly 13 comprises two back-to-back photosensors 30 and 11 having an aperture 33, the upper one 30 comprising at least four segments 30a–30d and the lower one 11 comprising at least four segments 11a–11d. Each segment is connected to signal conditioning hardware 21 conductors 31a–31e and 11a–11e shown in FIGS. 2 and 2A. Each such photosensor can be obtained, for example, from Silicon Detector Corp., Camarillo, California (part no. SD150-41). While the signal conditioning circuitry 21 can be any suitable circuit known to those skilled in the art or available commercially, a preferred signal conditioning device comprises a circuit for comparing received signals. The signal conditioning hardware 21 preferably includes circuitry for two kinds of comparisons: one, a comparison among the signals from the segments of the single photosensor and another for comparing the total signal from the upper photosensor of a back-to-back pair with the total signal from its lower back-to-back counterpart.

Beams at 14 and 28 are located on the optical axis of the instrument. Part of the power contained in the beam traveling downward along line 28 is intercepted by photosensor 30. If the normal of the target surface 23 coincides with the optical axis defined by line 28, and if the surface 23 is at a calibrated standoff distance from the instrument represented by the surface at the position 23 in FIG. 1, then the reflected light from the surface 23 travels along axis 28 through aperture 32, back again along lines 26, 24, 22 and 16 in a clockwise direction, and at 14 toward the light source 10. While passing up through aperture 33, the part of the optical power contained within the reflected beam is intercepted by photosensor 11 that faces surface 23 under examination. The standoff distance of the instrument is defined as the distance between two points: the first point identified by numeral 23a created by the intersection of lines 28 and 22 and the second point identified by numeral 27 created by the intersection of line 26 with the lower reflective surface of mirror 9.

FIG. 1 shows an optical lens identified by numeral 41. The photosensor assembly 13 connections to signal conditioning hardware 21 are represented by a single line 31. The light source 10 connections to the signal conditioning hardware 21 are also identified by a single line numeral 34.

The operation of the instrument will now be described. If the normal of surface 23 coincides with the optical axis 28 and if the distance between point 23a of surface 23 and point 27 is equal to the standoff distance as previously defined, then upper photosensor 30 will intercept a portion of the optical power contained within the beam traveling downwardly along axis 28. The portion of the beam intercepted by photosensor 30 forms a ring-shaped light spot identified by numeral 28 in FIG. 2. If, however, the surface 23 is displaced downwardly toward a line represented by numeral 25 while the normal of the of the surface is parallel to the optical axis 28, the normal of the surface 23 and the beam traveling downwardly along line 22 will intersect the surface at its new location at point 25a. The beam will then be reflected along lines 36, 38 and 40. As a result of change in surface position from 23 to 25, the ring-shaped light spot will move horizontally leftward on the face of photosensor 30 to a position indicated by dotted lines and numeral 40 in FIG. 2. Likewise, if the surface 23 under evaluation is displaced upwardly above point 23a in FIG. 1, the light spot will move horizontally to the right (not shown) on photosensor 30. If the normal of the surface represented by line 25 does not coincide with the optical axis 28 while maintaining the standoff distance between surface and instrument, the light spot will change position radially of the photosensor 30, depending upon the angle to which the instrument is tipped. Likewise, if the distance between the instrument and surface under evaluation is not equal to the standoff distance, and if the optical axis 28 of the instrument does not coincide with the normal of the surface, the light spot will move on the face of photosensor 30 as a function of surface relative displacement from the standoff distance and the angular displacement of the normal of the surface 23 from the optical axis 28 of the instrument. Therefore, because of the variation in the relative strength of the currents through lines 31a-31e to the signal conditioning hardware 21, the instrument provides the capability of maintaining a predetermined standoff distance between the instrument and surface 23 under evaluation in such a way that the optical axis 28 of the instrument coincides with the normal of the surface 23 under evaluation. To accomplish this, only one radially segmented apertured photosensor 30 is used. If desired, the function of proper standoff position determination can be performed by a radially segmented photosensor without an aperture 33. Once the distance between the instrument and the surface 23 under evaluation is equal to the standoff distance, the beam reflected from surface 23 along axis 28 represents the reflectance of surface 23 around a point 23a. The radially segmented apertured photosensor 13 intercepts a portion of this reflectance.

The photosensor assembly 13 includes upper and lower back-to-back segmented photosensors 30 and 11 with a central aperture 33. The measured characteristic of the specimen 23 is the reflectance of the specimen. This is measured as a function of the difference between the signals obtained from the upper photosensor 30 receiving light from source 10 and the signals from the lower photosensor 11 which receive diffused light reflected directly from the specimen onto the lower photosensor. The signal conditioning hardware 21 that is connected to the photosensor assembly 13 provides information about both the displacement of surface 23 from the standoff distance of the instrument and the displacement of the normal of surface 23 from the optical axis 28 of the instrument, and the reflectance characteristic of surface 23 around point 23a.

Figure 3:
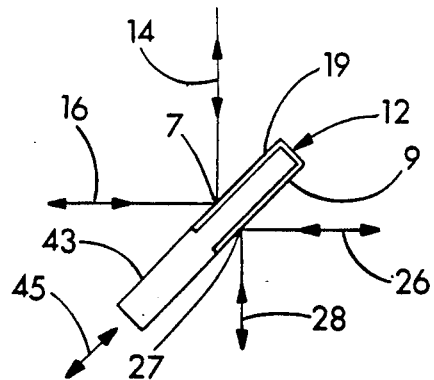
FIG. 3 is a detailed side elevational view of a double-sided mirror assembly.
Figure 3A:
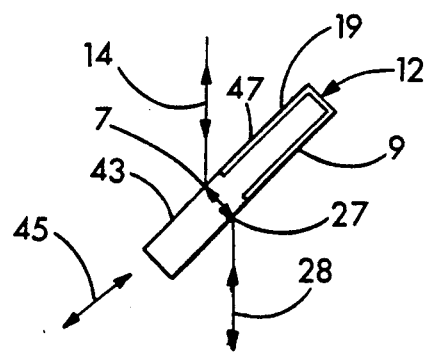
FIG. 3a is a detailed side elevational view of a double-sided mirror assembly.

FIGS. 3 and 3a illustrate one example of a double-sided mirror assembly 12 and its effect on the beam path. FIG. 3 shows an expanded view of the double-sided mirror and its interaction with the beam traveling along lines 14, 16, 26 and 28. The mirror layers 9 and 19 are deposited on glass plate 43. When desired, the double-sided mirror assembly 12 is displaced along the line represented by numeral 45. The thickness of the glass plate 43 and its index of refraction should be such that their combined effect on the beam traveling along line 14 will provide an optical path connection represented by a refracted beam line 47 between dimensional reference point 7 and point 27 to carry the beam downwardly along the optical axis at 28.

To avoid interception of diffused reflectance resulting from angular illumination of surface 23 by the beam that travels along line 22 once the surface is properly positioned in relationship to the instrument, one displaces the double-sided mirror assembly 12 from the position of FIG. 3 to the position of FIG. 3a. The displacement of double-sided mirror assembly 12 can be accomplished manually, electromechanically or by several other means. Once the mirror assembly 12 is displaced, the beam from light source 10 will pass straight down along line 14 and through diffraction with the glass layer along line 47 will continue to travel along the optical axis 28 without encountering lateral, i.e. non-axial, mirrors 18 and 20.

Mirrors 18 and 20 are shown as plane stationary mirrors only for the sake of example. The mirrors can have different shapes and can be mechanized in many different ways, e.g. by tilting them simultanesoulsy to different angles other than the angle $\beta$ to create a variable standoff distance.

FIG. 2 shows the preferred minimal number of segments (four) used (30a–30d) to properly position the surface 23 in relation to the instrument. Conductors 31a–31d carry the signals produced by respective segments to the signal conditioning hardware 21. These signals are proportional to the optical power received by by the respective segments 30a–30d. Conductor 31e represents a signal return conductor for photosensor 30, which is common to all segments. Likewise, as shown in FIG. 2A, beneath photosensor 30 is the radially segmented apertured photosensor 11 that is mounted in a back-to-back relationship to photosensor 30. The photosensor 11 has four segments 11a–11d and five contacts 31f–31j which operate in the same way as in the photosensor 30.

Refer now to FIG. 1a for the description of the instrument of the present invention when made to employ interferometric principles and wherein the same numerals correspond to parts already described. For the time being, assume that the distance between surface 23 under evaluation and the instrument is equal to the standoff distance of the instrument and that the normal of the surface 23 coincides with the optical axis 28 of the instrument. The instrument has the same mirrors 18 and 20 and the same photosensor assembly 13. Numeral 49 designates a beam splitter (which replaces the double-sided mirror assembly in FIG. 1) positioned at a 45° angle to the optical axis coinciding with light of the beam from the source 10 on line 14. For the sake of simplicity, the beam splitter 49 is identified by a single line. The beam from the coherent light source 10 travels along line 14 through an optional but preferred optical isolator 67 and through an upper segmented double-sided photosensor assembly 59 to beam splitter 49. The photosensor assembly 59 is connected to signal conditioning hardware 70 by conductors designated generally by numeral 61.

Signal conditioning hardware 70 has suitable circuitry for comparing the currents from the segments of the photosensor 59 and includes common elements and components of the same kind used in signal conditioning hardware 21 of FIG. 1. The signal conditioning hardware 70 provides circuitry for comparison of interference signals resulting from the difference between optical paths, as will be described.

In case the light source 10 is a laser diode or other laser and its coherence may deteriorate as a function of the reflected light into it, the optical isolator 67 (such as a Faraday type isolator) will prevent such coherence damaging reflections from entering the light source 10. At a dimensional reference point 7 that is established by the intersection of beam splitter 49 with the optical axis 28 of the instrument on line 14, the beam is divided into two parts. One part travels leftward along line 16 and the other travels downward along the axis 28. The beam that travels leftward follows a general counterclockwise direction as described by lines 16, 22, 24 and 26. While it cycles along lines 16, 22, 24 and 26 during each such cycle, it is subjected to periodic splits by beam splitter 49 that directs a portion of counterclockwise cycling beam downward along the path of line 28, the optical axis of the instrument. Thus, there are created two beams of different optical path lengths that travel downward along axis 28: the counterclockwise circulating path and the path directly from the source 10. A portion of the power contained within these two interfering beams is intercepted by photosensor 30. The combined signal sensed by the upper photosensor 30 is an optical interference pattern created by the difference in the optical path lengths between a beam that travels straight downward from light source 10 and the beam traveling in a counterclockwise direction while subjected to periodic splits downward. The portion of both of these beams that continues to travel along line 28 to surface 23 is reflected upwardly along axis 28. A portion of the two interfering beams that are reflected upwardly from surface 23 is intercepted by photosensor 11, and the remaining portion travels upwardly to the beam splitter 49 where the two interfering beams are split. One part of the two beams travels upward along line 14 and the reflected part travels along lines 26, 24, 22 and 16 in a clockwise direction, in which the beams are continuously cycling while subjected to periodic splits by beam splitter 49. During each such split a portion of the beam travels along line 14 upwardly through the photosensor assembly 59, which can be identical to photosensor assembly 13. The lower surface 71 of photosensor assembly 59 intercepts a portion of the optical power of the beams traveling upwardly along line 14. There are two types of beams that travel upwardly and are intercepted by the photosensor assembly 59: the interfering beams that travel upwardly from point 23a straight through beam splitter 49, and second, the portion of the interfering beams that cycle in a clockwise direction. These two sets of beams have different optical path lengths. The additional interference due to the difference in optical light path lengths between these two sets of beams will be sensed by the lower surface 71 of photosensor assembly 59. In this embodiment, one of the photosensors is a lower photosensor assembly 13 positioned between the beam splitter 49 and the specimen. The lower photosensor assembly 13 comprises a photosensor assembly having a pair of upper 30 and lower 11 back-to-back segmented photosensors with aligned apertures. The lower photosensor 13 receives interference beams that are reflected upwardly from the target surface 23.

Any deviation of surface 23 and its normal from the standoff distance and the optical axis will alter the interference characteristics as sensed by photosensor assemblies 13 and 59. For standoff distance position acquisition, one can use single-sided apertured segmented photosensor 30 and 71, although double-sided assemblies such as 13 and 59 improve overall accuracy and can indicate changes in beam polarization, for example. The difference between the optical power received by the upper photosensor 59 and lower photosensor 13 is compared to indicate the reflectance of the specimen as a function of the optical power reflected directly from the specimen along the optical axis onto the lower photosensor of the pair.

Refer now to optional components 73–79 which can be used in another embodiment of an instrument based on the reflective/refractive method illustrated in FIG. 1 to obtain reflectance measurements at other than standoff distances. As shown below, the double-sided mirror assembly 12 on axis 28 is a beam splitter 79 which is positioned in a noncoplanar configuration with double-sided mirror assembly 12. An additional collimated light source 73 projects a beam along line 77. The beam is split into two parts. The part of interest is directed by beam splitter 79 along the optical axis 28 downwardly to surface 23. Assuming the instrument is properly aligned with the surface, i.e. that the normal of surface 23 coincides with the optical axis 28, the beam will be reflected from surface 23 along optical axis 28. Part of the reflected beam is intercepted by photosensor 11; the rest of the beam passes through the aperture 33 of photosensor assembly 13 to beam splitter 79. Light source assembly 73 is connected by conductors 75 to signal conditioning hardware 21. Signal conditioning hardware 21 also controls the turn on/off sequence of light sources 10 and 73. For example, when light source 73 is on, light source 10 is off and vice versa.

Signal conditioning hardware 21 also provides reflectance information as sensed by photosensor 11 and position information of surface 23 as sensed by the photosensor 13. Therefore, regardless of the use of beam splitter 79 and light source 75, in this case the photosensor 30 measures distance based primarily on specular reflectance. The amount of light intercepted by photosensor 30 is proportional primarily to specular reflection as induced by angular illumination ($\beta$). Photosensor 11 measures primarily diffused reflectance that results from normal illumination along line 28.

Many variations of the present invention within the scope of the appended claims will be apparent to those skilled in the art once the principles described above are understood.

What is claimed is:

1. An optical instrument for measuring characteristics of a specimen comprising, a light source, an axial reflective member spaced from the light source to define an optical axis for the instrument along a line between the light source and the reflective member, a non-axial reflector positioned laterally of the reflective member and laterally of the optical axis to receive a beam reflected from the axial reflective member, said non-axial reflector being oriented to reflect the beam onto the specimen, a photosensor, a second non-axial reflector to receive the beam reflected from the specimen and reflect it onto the photosensor, said photosensor being positioned in the instrument to receive the beam from the second non-axial reflector, and means for carrying signals from the photosensor to signal conditioning hardware means to provide information concerning the specimen responsive to said signals from said photosensor.

2. The instrument of claim 1 wherein the beam reflected from the second non-axial reflector is reflected thereby toward the optical axis of the instrument, an additional axial reflector means is provided to receive the beam from the second non-axial reflector and reflect said beam along the optical axis of the instrument onto said photosensor.

3. The optical instrument of claim 1 wherein the photosensor is segmented and the means for carrying signals from the photosensor to signal conditioning hardware comprises a conductor connected to each segment of the photosensor for carrying current to the signal conditioning hardware means and for completing an electrical circuit through the photosensor means and said signal conditioning hardware means is adapted to compare signals from the segments of the photosensor to provide information concerning the position of the specimen.

4. The optical instrument of claim 1 wherein the photosensor means is a photosensor assembly having upper and lower photosensors with a central aperture and the measured characteristic of the specimen is the reflectance of the specimen measured as a function of the difference between the signals obtained from the upper photosensor which receives light directly from the light source and the signals from the lower photosensor which receives light reflected from the specimen onto the lower photosensor.

5. The optical instrument of claim 1 wherein the measured characteristics comprise the difference between a standoff distance defined by the distance between a) the intersection of the optical axis and the beam from the second non-axial reflector and b) the specimen as a function of the displacement of the beam across the surface of the photosensor so as to produce changes in the optical power received by the segments of the photosensor.

6. The optical instrument of claim 1 wherein the axial reflective member is a beam splitter and said instrument includes a pair of said photosensors, said photosensors are each provided with a central aperture aligned on the optical axis of the instrument on opposite sides of the beam splitter to receive interfering beams traveling away from the beam splitter in opposite directions along the optical axis of the instrument.

7. The instrument of claim 1 wherein the photosensor is positioned between the axial reflective member and the specimen and said photosensor includes a pair of upper and lower back-to-back photosensors having aligned apertures and the difference in the optical power received by the upper and lower photosensors is compared to indicate the reflectance of the specimen as a function of the optical power reflected directly form the specimen along the optical axis onto the lower photosensor of the pair of compared to the optical power from the light source striking the upper photosensor of said pair.

8. The optical instrument of claim 1 wherein an additional light source is provided, an additional axial reflective means is provided in a position to reflect light from the additional light source through said aperture in said photosensor onto said surface of said specimen, and means to operate said light sources alternately or at desired sequences to obtain reflectance measurements at distances other than standoff distances.

9. The optical instrument of claim 1 wherein there are two laterally aligned non-axial reflectors on opposite sides of the axial reflective member.

10. The optical instrument of claim 9 wherein the non-axial reflectors are adjustable to vary the angular relationship of each to establish variations in a standoff distance for said instrument.

11. The optical instrument of claim 1 wherein the axial reflective member is a double-sided mirror and the photosensor is positioned between the double-sided mirror and the specimen.

12. The optical instrument of claim 11 wherein he mirror is shiftable to a position to which reflective material thereon is displaced out of the optical axis of the instrument, allowing light from the source to pass the mirror.

13. The optical instrument of claim 11 wherein the double-sided mirror is movable mounted and adapted to be displaced toward one side to allow light to travel directly from the light source to the specimen when desired.

14. An optical instrument for measuring characteristics of a surface of a specimen comprising, a source of light, said instrument directing a beam of light from the source obliquely at a selected angle $\beta$ to an optical axis positioned normal to the surface of the specimen, said specimen reflecting the light beam from the surface to provide a reflected beam having the same angle β to the optical axis, a first reflective means for deflecting the reflected beam centrally toward the optical axis, a second reflective means for deflecting the centrally directed beam along said optical axis toward the specimen, photosensor means positioned to receive light from the beam after being reflected from the specimen to measure characteristics of the specimen, the beam from the second reflective means being positioned normal to the surface of the specimen to define the location of said optical axis of the instrument, the oblique beam directed from the source toward the specimen intersecting said optical axis and intersecting said surface of the specimen at a selected point when the instrument is at a selected standoff distance from the instrument, but when the specimen is moved toward or away from the instrument on said optical axis in either direction or is tilted, the beam reflected from the specimen is displaced thereby, and a photosensor positioned to detect the displaced beam when the surface of the specimen is moved to a position other than the standoff distance from the instrument or tilted with respect to a line normal to the surface of the specimen.

15. The optical instrument of claim 14 including an additional light source for illuminating the specimen along said optical axis and photosensor means receiving a beam of light reflected from the specimen and originating from the additional light source for determining reflective characteristics of the specimen.

16. The optical instrument of claim 14 wherein the instrument has a pair of aligned back-to-back segmented photosensors optically positioned between one of said reflective means and the surface of the specimen.

17. The optical instrument of claim 16 wherein the back-to-back photosensors are apertured and the aperture is positioned at the optical axis of the instrument.

18. The optical instrument of claim 14 wherein said photosensor means is optically positioned between the light source and the surface of the specimen being illuminated.

19. The optical instrument of claim 18 wherein the photosensor means comprises a pair of segmented photosensors in back-to-back relationship.

20. The optical instrument of claim 19 wherein the back-to-back photosensor means are apertured and the aperture is positioned so that the beam from the light source passes therethrough.

21. An optical instrument for measuring the characteristics of a specimen having a light reflective surface comprising, a light source, said instrument having an optical axis positioned normal to the reflective surface of the specimen, the instrument directing a beam for the light source onto the specimen at an oblique angle β relative to said optical axis, the optical axis and the oblique beam of light from the light source intersecting at a point which defines a standoff distance from the instrument, photosensor array means positioned to receive said beam of light after being reflected from the specimen at an inclined angle β to the optical axis when said received beam is in a first position, said specimen and instrument being movable relative to one another along the optical axis, the photosensor array means being constructed and arranged to detect movement of the reflected beam from its first position responsive to changes in the standoff distance that alters the point at which the reflected beam strikes the photosensor array means, said photosensor array mans thereby sensing changes in the location of the beam impinging thereon whereby the deviation between the position of the specimen and the standoff distance can be determined from the displacement of the beam on the photosensor array means.

22. The optical instrument of claim 21 wherein said photosensor array is constructed to measure the optical power of the light from the light source that has been reflected from the specimen onto the photosensor array to thereby determine the reflectivity of the specimen.

23. The optical instrument of claim 21 wherein said photosensor array means includes a pair of back-to-back apertured photosensors including one photosensor positioned to receive said reflected inclined beam and one positioned to receive a beam reflected from the specimen along the optical axis, and a photosensor including a pair of apertured back-to-back photosensors optically positioned between said light source and the specimen for comparing light from the source with a beam reflected from the specimen.

24. The optical instrument of claim 23 wherein a second light source is provided, said pair of photosensors is constructed to measure the optical power of the light projected from said light sources and to measure the corresponding optical power that has been reflected from the specimen onto said pair of photosensors to thereby determine the reflectivity of the specimen at two angles of illumination, namely, normal and oblique illumination.

25. An optical instrument to be used for projecting a beam of light onto a specimen and for evaluating the specimen, said instrument comprising,
a source of light,
said instrument directing a beam of light from the source of light obliquely onto the specimen, said specimen reflecting the light beam from the surface thereof to provide an oblique reflected beam, said instrument having an optical axis normal to the specimen,
means for deflecting said reflected beam toward the specimen along the optical axis,
photosensor means positioned to intercept one of said beams and being located to receive said beam of light reflected from said specimen for detecting a characteristic of the light received from the specimen, and
the photosensor means has means permitting two-way transmission of light past itself proceeding both toward and away from said photosensor in opposite directions when the light source is energized.

26. The optical instrument of claim 25 wherein said photosensor means comprises a pair of apertured back-to-back photosensors.

27. The optical instrument for measuring characteristics of a surface of a specimen comprising,
a light source for illuminating a specimen adapted to reflect at least some of the light incident thereto,
said instrument including means for directing an outbound beam of light proceeding from the source to the specimen and striking the specimen at a predetermined oblique angle incident thereto, said outbound beam being reflected from the specimen to provide an oblique reflected outbound beam proceeding away from the specimen at the same angle of reflection as the oblique beam incident to the specimen,
means for directing the reflected outbound beam back toward the specimen so as to strike the specimen along an optical axis normal to the surface of the specimen and the beam normal thereto then being reflected from the specimen as a returning beam that travels back toward the light source in the opposite direction from the outbound beam, and a photosensor means interposed in the path of the outbound and returning beams for sensing a characteristic of light incident thereto.

28. The optical instrument of claim 27 wherein the photosensor means is segmented so as to include a plurality of separate sensing elements.

29. The apparatus of claim 27 wherein the photosensor means comprises a pair of apertured back-to-back photosensors, each adapted to sense a characteristic of light striking an exposed surface thereof.

* * * * *